United States Patent [19]

Price et al.

[11] 4,223,159

[45] Sep. 16, 1980

[54] BY-PRODUCT RECYCLING PROCESS

[75] Inventors: John A. Price, Kingston, N.J.; Edward F. Orwoll, Langhorne, Pa.

[73] Assignee: FMC Corporation, Philadelphia, Pa.

[21] Appl. No.: 33,607

[22] Filed: Apr. 26, 1979

[51] Int. Cl.$^2$ .............................................. C07C 69/52
[52] U.S. Cl. ................................... 560/205; 560/217; 560/225
[58] Field of Search ....................... 560/205, 217, 218

[56] References Cited

U.S. PATENT DOCUMENTS

| | | | |
|---|---|---|---|
| 3,056,817 | 10/1962 | Werber et al. | 560/217 |
| 3,636,268 | 8/1972 | Jobert et al. | 560/217 |
| 3,784,578 | 1/1974 | Swodenk et al. | 560/217 |

OTHER PUBLICATIONS

Groggins, O. H. et al. "Unit Processes in Organic Synthesis," pp. 696–697, 5th Ed. (1958), McGraw Hill, Publ.

Kondo, Kiyosi et al., "New Synthesis of the Acid Moiety of Pyrethroids," pp. 128–136 of ACS Symposium Series 42, Synthetic Pyrethriods, Elliott, Michael, Ed. (1976).

Primary Examiner—Natalie Trousof
Assistant Examiner—L. Hendriksen
Attorney, Agent, or Firm—Richard L. Hansen; Henry R. Ertelt

[57] ABSTRACT

3-Methyl-2-butenyl 3,3-dimethyl-4-pentenoate, by-product in the condensation between 3-methyl-2-butene-1-ol and a lower alkyl orthoacetate, can be recycled into the condensation by alkoxylating it with a lower alkyl alcohol or orthoacetate in the presence of a basic ester exchange catalyst.

11 Claims, No Drawings

BY-PRODUCT RECYCLING PROCESS

This invention is in the field of chemical processes; more specifically, the beneficiation and recycling of the by-product from a chemical process, thereby increasing the overall yield of the desired product and avoiding disposal of the by-product.

U.S. Pat. No. 4,024,163 discloses a series of new pyrethroid insecticides. These insecticidal esters are characterized by chemical structures containing a 3-(2,2-dihalovinyl)-2,2-dimethylcyclopropanecarboxylic acid unit. These acid units may be prepared in several ways; one of these methods is disclosed by Kondo et al. in "Synthetic Pyrethroids," Michael Elliott, Editor, Americal Chemical Society, Washington, D.C., 1977, pp 128-136.

The synthesis of Kondo et al. involves several chemical process steps. In the first step, 3-methyl-2-buten-1-ol is condensed with a lower alkyl, orthoester, generally in the presence of an acid catalyst, to produce a lower alkyl 3,3-dimethyl-4-pentenoate ester. This condensation proceeds via reactive intermediates, such as a 1-(1,1-di(lower alkoxy)ethoxy)-3-methyl-2-butene and a 1,1'-[1-(lower alkoxy)ethylidenebis(oxy)]bis[3-methyl-2-butene], and formally requires the elimination of two moles of lower alkyl alcohol from the reactants and molecular rearrangement of an intermediate condensation product (a Claisen rearrangement). Wherever used herein the term "lower," modifying alkyl, akloxy, and alkoxide, for example, means $C_1$-$C_6$, preferably $C_1$-$C_4$.

The condensation is not clean-cut, however. For example, three moles of lower alkyl alcohol can be eliminated from the reactants to produce the undesired by-product, 3-methyl-2-butenyl 3,3-dimethyl-4-pentenoate. This by-product is higher-boiling than the reactants and desired product and typically remains as a residue in the reaction vessel after the desired ester is removed by distillation. To the extent that this by-product is produced, the yield of the desired ester is decreased, safe disposal of the by-product without contaminating the environment presents a problem, and the overall cost of the process is higher.

Therefore, the object of this invention is to provide an improvement in the condensation process which recycles the by-product to the desired ester.

According to one embodiment of this invention, in a process for condensing 3-methyl-2-buten-1-ol and a lower alkyl orthoacetate to produce a crude product containing the desired lower alkyl 3,3-dimethyl-4-pentenoate ester and 3-methyl-2-butenyl 3,3-dimethyl-4-pentenoate, this invention is the improvement which comprises alkoxylating the crude product with at least one alkoxylating agent selected from lower alkyl alcohols and orthoacetates in the presence of a titanium lower alkoxide catalyst, producing more of the desired lower alkyl 3,3-dimethyl-4-pentenoate from the 3-methyl-2-butenyl 3,3-dimethyl-4-pentenoate.

According to a preferred embodiment of this invention, in a process for condensing 3-methyl-2-buten-1-ol and a lower alkyl orthoacetate to produce the desired lower alkyl 3,3-dimethyl-4-pentenoate ester, removing the desired ester by distillation, leaving a residue containing 3-methyl-2-butenyl 3,3-dimethyl-4-pentenoate, this invention is the improvement which comprises alkoxylating the residue with at least one alkoxylating agent selected from lower alkyl alcohols and orthoacetates in the presence of a basic ester exchange catalyst to yield as product the desired ester together with one or more of 3-methyl-2-buten-1-ol, a 1-(1,1-di(lower alkoxy)ethoxy)-3-methyl-2-butene, and a 1,1'-[1-(lower alkoxy)ethylidenebis(oxy)]bis[3-methyl-2-butene] and recycling the product as starting material in the process.

Although a certain amount of the undesired 3-methyl-2-butenyl 3,3-dimethyl-4-pentenoate is produced no matter which lower alkyl orthoacetate is employed in the condensation, the amount of this by-product is especially large when trimethyl orthoacetate is used. Therefore, the improvement of this invention is especially desirable when the condensation is between 3-methyl-2-buten-1-ol and trimethyl orthoacetate.

A basic catalyst is required in alkoxylating the 3-methyl-2-butenyl 3,3-dimethyl-4-pentenoate residue from which the desired ester has been removed by distillation. Suitable catalysts are known in the art as ester exchange catalysts. These catalysts include, for example, alkali metal hydroxides and lower alkoxides as well as titanium lower alkoxides. In selecting an alkoxide catalyst, it is desirable, but not necessary, to maintain the same alkoxy group in the catalyst and in the alcohol or orthoacetate to avoid the formation of side-products. Although the amount of catalyst is not critical, it is desirable, both when alkoxylating the crude condensation product and the distillation residue, to use about 0.5-20 mole percent of catalyst based on the amount of 3-methyl-2-butenyl 3,3-dimethyl-4-pentenoate, especially about 1-10 mole percent. Additional base is required if the condensation employed an acid catalyst, as is generally the case, in order to neutralize the acid. It is usually most convenient to use for this purpose the same base to be employed in the subsequent alkoxylation. When the crude condensation product is to be distilled before alkoxylating the residue, the crude product should be neutralized before the distillation.

When a lower alkyl alcohol is the alkoxylating agent for the distillation residue, an alkali metal alkoxide is the preferred catalyst; when a lower alkyl orthoacetate is the alkoxylating agent, a titanium alkoxide is especially preferred.

The lower alkyl alcohol or orthoacetate is generally employed in equimolar to 20-fold molar excess amounts with respect to the 3-methyl-2-butenyl 3,3-dimethyl-4-pentenoate. Part of the excess alcohol and all of the orthoacetate are not wasted when the distillation residue is alkoxylated, since the excess reactants, together with the recycled residue, are starting materials for the next condensation or alkoxylation.

Although the alkoxylation can be carried out at lower temperatures, for example, 0° C., for reasonable rates, it should be conducted in the range of about 20°-200° C. Temperatures in the range 125° C.-175° C. are preferred when the alkoxylating agent is a lower alkyl orthoacetate, but lower temperatures, in the range 20° C.-125° C. may be employed and are preferred when a lower alkyl alcohol is the alkoxylating agent. Depending upon the reactants and the temperature employed, it may be desirable to conduct the reaction under pressure.

It is preferred, however, that the alkoxylation of the distillation residue from condensing 3-methyl-2-butenol and trimethyl orthoacetate be carried out at atmospheric pressure. This can best be done by employing as the alkoxylating agent a mixture of methanol, preferably in 5 to 10-fold molar excess amount with respect to the 3-methyl-2-butenyl 3,3-dimethyl-4-pentenoate, and trimethyl orthoacetate. An alkali metal methoxide, especially 2-5 mole percent sodium methoxide, is the preferred catalyst, the largest excess of methanol requiring the most catalyst. A temperature between 20° C. and 90° C. is preferably employed.

This invention will be understood more completely by reference to the following Examples.

EXAMPLE 1

Reaction of 3-methyl-2-butenyl 3,3-dimethyl-4-pentenoate with methyl alcohol using titanium tetraisopropoxide catalyst Samples of a solution of 3-methyl-2-butenyl 3,3-dimethyl-4-pentenoate(9.8 g, 0.050 mole), methanol (16.0 g, 0.500 mole), and 0.15 ml of titanium isopropoxide (approximately 0.0005 mole) were charged to stainless steel tubes. The sealed tubes were placed in an oil bath at 150° C., and samples were withdrawn at intervals for analysis. At the end of seven hours the mixture contained 19.8% methyl 3,3-dimethyl-4-pentenoate, 13.7% 3-methyl-2-butenol, and 2.0% 3-methyl-2-butenyl 3,3-dimethyl-4-pentenoate (before reaction, the mixture contained 28%) based on glpc analysis.

EXAMPLE 2

Reaction between 3-methyl-2-butenyl 3,3-dimethyl-4-pentenoate and 1,1,1-trimethoxyethane using titanium tetraisopropoxide catalyst Samples of a solution of 3-methyl-2-butenyl 3,3-dimethyl-4-pentenoate (4.90 g, 0.025 mole), 1,1,1-trimethoxyethane (30.6 g, 0.25 mole), and titanium tetraisopropoxide (0.28 g, 0.001 mole) were charged to stainless steel tubes. The sealed tubes were placed in an oil bath at 150° C., and a tube was periodically removed for analysis by glpc. The samples were heated for a total of 20 hours. At the end of this time the solution contained 74% 1,1,1-trimethoxyethane, 19% methyl 3,3-dimethyl-4-pentenoate, 1.5% methyl acetate, 3.5% methanol, 0.36% 3-methyl-2-butenyl acetate, 0.06% 3-methyl-2-butenol, and 0.1% 1-(1,1-dimethoxyethoxy)-3-methyl-2-butene.

EXAMPLE 3

Reaction of 3-methyl-2-butenyl 3,3-dimethyl-4-pentenoate with methyl alcohol using potassium hydroxide catalyst A mixture of 3-methyl-2-butenyl 3,3-dimethyl-4-pentenoate (19.6 g, 0.100 mole), methanol (16.7 g), and 10% potassium hydroxide in methanol (1.12 g) was stirred for 70 hours at room temperature. The mixture was then analyzed by glpc and found to contain 26% methyl 3,3-dimethyl-4-pentenoate, 19% 3-methyl-2-butenol, and 5.9% 3-methyl-2-butenyl 3,3-dimethyl-4-pentenoate.

EXAMPLE 4

Reaction of 3-methyl-2-butenyl 3,3-dimethyl-4-pentenoate with ethyl alcohol using sodium ethoxide catalyst A solution of 3-methyl-2-butenyl 3,3-dimethyl-4-pentenoate (19.6 g, 0.10 mole), ethanol (24.4 g, 0.53 mole), and 18% sodium ethoxide (1.14 g, 0.003 mole) in ethanol (0.02 mol) was prepared, allowed to stand at room temperature, and analyzed periodically by glpc. After 144 hours, the mixture contained 30% ethyl 3,3-dimethyl-4-pentenoate and 16% 3-methyl-2-butenol.

EXAMPLE 5

Reaction of 3-methyl-2-butenyl 3,3-dimethyl-4-pentenoate with methyl alcohol using sodium methoxide catalyst Samples of a solution of 3-methyl-2-butenyl 3,3-dimethyl-4-pentenoate (19.6 g, 0.10 mole), methanol (17.3 g, 0.54 mole), and sodium methoxide (0.43 g, 0.002 mole) in methanol (0.01 mole) were charged to stainless steel tubes. The sealed tubes were placed in an oil bath at 140° C., and a tube was removed periodically for analysis by glpc. After six hours the solution contained 33% methyl 3,3-dimethyl-4-pentenoate, 20% 3-methyl-2-butenol, and 7.3% 3-methyl-2-butenyl 3,3-dimethyl-4-pentenoate.

EXAMPLE 6

Reaction of 3-methyl-2-butenyl 3,3-dimethyl-4-pentenoate with a mixture of methanol and trimethyl orthoacetate using sodium methoxide catalyst, followed by the condensation of 3-methyl-2-butenol and 1,1,1-trimethoxyethane in the presence of the reaction product This reaction was one of a series of 20 batches in which the residual 3-methyl-2-butenyl 3,3-dimethyl-4-pentenoate from the previous reaction was alkoxylated and the product recycled as starting material for the next reaction.

The distillation residue from the previous reaction (12.4 kg), containing 81.5% 3-methyl-2-butenyl 3,3-dimethyl-4-pentenoate (55.4 moles) and 13.4% methyl 3,3-dimethyl-4-pentenoate (11.7 moles), was combined with 6.35 kg of tap water, agitated while cooling to 0°–5° C. (to remove neutralization salts), and separated.

To the organic layer was added 1,1,1-trimethoxyethane (42.2 kg, 351 moles) and three impure cuts of distillate from the previous reaction: one weighing 32.9 kg, containing 64.2% 1,1,1-trimethoxyethane (176 moles) and 25.1% methanol (258 moles), the second weighing 9.98 kg, containing 2.9% of 1,1,1-trimethoxyethane (2.4 moles) and 82.2% methanol (256 moles), and the third weighing 2.6 kg, containing 56.7% 1,1,1-trimethoxyethane (1.5 moles) and 31.4% methyl 3,3-dimethyl-4-pentenoate (0.268 mole). The mixture was heated to reflux in 30 minutes and refluxed for two hours to remove trace moisture by reaction with 1,1,1-trimethoxyethane. A small amount of methanol (3.6 kg) was removed by distillation during this time in order to maintain a pot temperature of 70°–75° C.

The mixture was cooled to 50°–60° C., and 25% sodium methoxide (557 g, 2.58 moles) in methanol (13 moles) was added. The resultant mixture was heated to reflux in fifteen minutes and refluxed for two hours at 76°–80° C. While refluxing continued, 85% phosphoric acid (297 g, 2.58 moles) was added to neutralize the sodium methoxide. A total of 5.0 kg of methanol was then removed by distillation, and the reaction mixture was analyzed by glpc and found to contain 14% methanol, 67% 1,1,1-trimethoxyethane, 9.6% methyl 3,3-dimethyl-4-pentenoate, 0.84% 3-methyl-2-butenol, 1.5% 1-(1,1-dimethoxyethoxy)-3-methyl-2-butene, and 1.3% 3-methyl-2-butenyl 3,3-dimethyl-4-pentenoate (representing 88% conversion).

Addition of 3-methyl-2-butenol (25.8 kg, 300 moles) containing 242 g of 85% phosphoric was begun and continued while 24.4 kg of distillate (mostly methanol) was removed. Distillation was continued and a second fraction was collected. The distillate in this fraction weighed 20.6 kg and consisted mainly of 1,1,1-trimethoxyethane. The mixture was then cooled to 50° C. and neutralized with 454 g of 25% sodium methoxide in methanol.

Distillation of the reaction mixture under reduced pressure (41–57 mm Hg) allowed recovery of the desired methyl 3,3-dimethyl-4-pentenoate. The first fraction, containing 53% of the desired ester, weighed 2.0 kg. The second fraction weighed 33.2 kg and contained 98.1% methyl 3,3-dimethyl-4-pentenoate (229 moles). The residue, weighing 13.4 kg, was washed with 6.8 kg of tap water, separated, and recycled essentially as described above.

At the completion of the 20 batch run, 50.3 moles of residual 3-methyl-2-butenyl 3,3-dimethyl-4-pentenoate remained; the rest of the residue, that from 19 batches, or about 1121 moles, was recycled to the desired product by the improvement of this invention. In the absence of the improvement, the residue would have required disposal.

EXAMPLE 7

Reaction of 3-methyl-2-butenyl 3,3-dimethyl-4-pentenoate in crude methyl 3,3-dimethyl-4-pentenoate with 1,1,1-trimethoxyethane using titanium tetraisopropoxide catalyst To a 25 gm. aliquot of the crude condensation product from reacting 3-methyl-2-butenol with trimethyl orthoacetate using a catalytic amount of phosphoric acid, neutralized with sodium methoxide, and containing (glpc) 67% methyl 3,3-dimethyl-4-pentenoate, 15% 3-methyl-2-butenyl 3,3-dimethyl-4-pentenoate, and 14% 1,1,1-trimethoxyethane, was added 0.25 ml of titanium tetraisopropoxide. Samples were charged to stainless steel tubes, and the tubes were placed in an oil bath at 150° C. Samples were withdrawn periodically and analyzed to determine the progress of the reaction. After 21 hours, 77% of the mixture was methyl 3,3-dimethyl-4-pentenoate, and 0.4% was 3-methyl-2-butenyl 3,3-dimethylpentenoate.

We claim:

1. In a process for condensing 3-methyl-2-buten-1-ol and a lower alkyl orthoacetate to produce the desired lower alkyl 3,3-dimethyl-4-pentenoate ester, removing the desired ester by distillation, leaving a residue containing 3-methyl-2-butenyl 3,3-dimethyl-4-pentenoate, the improvement which comprises alkoxylating the residue with at least one alkoxylating agent selected from lower alkyl alcohols and orthoacetates in the presence of a basic ester exchange catalyst to yield as product the desired ester together with one or more of 3-methyl-2-buten-1-ol and a 1-(1,1-di(lower alkoxy)ethoxy)-3-methyl-2-butene and recycling the product as starting material in the process.

2. The process of claim 1 wherein the basic ester exchange catalyst is selected from alkali metal hydroxides, alkali metal lower alkoxides, and titanium lower alkoxides.

3. The process of claim 2 wherein about 0.5–20 mole percent of catalyst based on the amount of 3-methyl-2-butenyl 3,3-dimethyl-4-pentenoate is used.

4. The process of claim 1 wherein the residue is alkoxylated with lower alkoxy orthoacetate in the presence of a titanium lower alkoxide catalyst.

5. The process of claim 1 wherein the residue is alkoxylated with lower alkyl alcohol in the presence of an alkali metal lower alkoxide catalyst.

6. The process of claim 1 wherein the alkoxylation is carried out at a temperature between 20° C. and 200° C.

7. In a process of claim 1 wherein 3-methyl-2-buten-1-ol is condensed with trimethyl orthoacetate, the improvement which comprises alkoxylating the residue with a mixture of methanol and trimethyl orthoacetate.

8. The process of claim 7 wherein the catalyst is sodium methoxide.

9. The process of claim 8 wherein about 1–10 mole percent sodium methoxide based on the amount of 3-methyl-2-butenyl 3,3-dimethyl-4-pentenoate is used.

10. The process of claim 9 carried out at a temperature between 20° C. and 90° C.

11. In a process for condensing 3-methyl-2-buten-1-ol and a lower alkyl orthoacetate to produce a crude product containing the desired lower alkyl 3,3-dimethyl-4-pentenoate ester and 3-methyl-2-butenyl 3,3-dimethyl-4-pentenoate, the improvement which comprises alkoxylating the crude product with at least one alkoxylating agent selected from lower alkyl alcohols and orthoacetates in the presence of a titanium lower alkoxide catalyst, producing more of the desired lower alkyl 3,3-dimethyl-4-pentenoate from the 3-methyl-2-butenyl 3,3-dimethyl-4-pentenoate.

* * * * *